United States Patent
Françon

(10) Patent No.: US 7,404,960 B2
(45) Date of Patent: Jul. 29, 2008

(54) MULTIVALENT VACCINE COMPOSITION HAVING INCREASED STABILITY OF CAPSULAR POLYSACCHARIDE

(75) Inventor: Alain Françon, Bessenay (FR)

(73) Assignee: Aventis Pasteur SA, Lyons (FR)

( * ) Notice: Subject to any disclaimer, the term of this patent is extended or adjusted under 35 U.S.C. 154(b) by 424 days.

(21) Appl. No.: 10/485,748

(22) PCT Filed: Jul. 31, 2002

(86) PCT No.: PCT/FR02/02770

§ 371 (c)(1),
(2), (4) Date: Feb. 3, 2004

(87) PCT Pub. No.: WO03/013600

PCT Pub. Date: Feb. 20, 2003

(65) Prior Publication Data

US 2004/0170648 A1    Sep. 2, 2004

(30) Foreign Application Priority Data

Aug. 8, 2001    (FR) .................................. 01 10573

(51) Int. Cl.
| | | |
|---|---|---|
| A61K 39/295 | (2006.01) | |
| A61K 39/112 | (2006.01) | |
| A61K 33/06 | (2006.01) | |
| A61K 33/08 | (2006.01) | |
| A01N 59/06 | (2006.01) | |
| A01N 63/00 | (2006.01) | |

(52) U.S. Cl. ............... 424/201.1; 424/226.1; 424/258.1; 424/682; 424/690; 424/698; 424/93.6

(58) Field of Classification Search ........................ None
See application file for complete search history.

(56) References Cited

U.S. PATENT DOCUMENTS 6,585,973 B1 *    7/2003    Lees ........................ 424/193.1

FOREIGN PATENT DOCUMENTS

| WO | WO 96 37222 | | 11/1996 |
|---|---|---|---|
| WO | WO 9637222 | * | 11/1996 |
| WO | WO 99 48525 | | 9/1999 |
| WO | WO 0012129 | * | 3/2000 |
| WO | 00/12129 | * | 9/2000 |
| WO | WO 0062801 | * | 10/2000 |

OTHER PUBLICATIONS

Havrix Monodose (Hepatitis A) Vaccine Patienti Information Leaflet. Available from GlaxoSmithKiline/SmithKline Beecham.*
Van Hoecke et al. 1998 J Travel Med 5:116-120.*
Adju-phos product monograph.*
Beran et al. 2000. J. Travel Med 7:246-252.*
Stroop. Feb. 2002 Carbohydrate Research 337:335-344.*
Strugess et al. 1999. Vaccine 17:1169-1178.*
Rinella et al. 1995. Journal of Colloid and Interface Science vol. 172 p. 121-130.*
Havrix product monograph 2001.*
Corbel, M.J. "Reasons for Instability of Bacterial Vaccines", *Dev. Biol. Stand.*, vol. 87, pp. 133-124. (1996).
Dumas, R., et al., "Safety And Immunogenicity Of A New Inactivated Hepatitis A Vaccine In Concurrent Administration With A Typhoid Fever Vaccine Or A Typhoid Fever + Yellow Fever Vaccine" *Advances in Therapy*, vol. 14, No. 4, pp. 160-167 (Jul./Aug. 1997).
Van Hoecke, C. et al., "Concomitant Vaccination against Hepatitis A and Typhoid Fever" *J. Travel. Med.* vol. 5, pp. 116-120 (1998).
Translation of PCT International Preliminary Examination Report, International Application No. PCT/FR2002/002770, International Filing Date: Jul. 31, 2002.

* cited by examiner

*Primary Examiner*—Patricia A. Duffy
*Assistant Examiner*—Oluwatosin Ogunbiyi
(74) *Attorney, Agent, or Firm*—McDonnell Boehnen Hulbert & Berghoff LLP

(57) ABSTRACT

A vaccine composition comprising two valences is provided: (i) a first valence which is adjuvant-enhanced with aluminum hydroxide and (ii) a second valence which contains a polysaccharide of bacterial capsule comprising one or more o-acetyl groups and which is not adsorbed with aluminum oxide due to the presence of a protecting compound which may be a phosphate, a citrate or a carbonate and which prevents the adsorption. The first valence can be any vaccine valence. In one particular embodiment, the vaccine composition contains (i) Hepatitis A valence, adsorbed on aluminum hydroxide and (ii) the typhoid fever valence formed by the polysaccharide Vi of the *Salmonella typhi* capsule.

10 Claims, No Drawings

MULTIVALENT VACCINE COMPOSITION HAVING INCREASED STABILITY OF CAPSULAR POLYSACCHARIDE

The present invention relates in particular to a stabilized bivalent hepatitis A/typhoid fever (HA-Vi) immunization composition in which the Vi valence conserves its immunogenic power for at least 24 months approximately.

Hepatitis A and typhoid fever are two diseases for which a vaccine already exists. They are both found in regions of the world where the hygiene conditions are far from optimal. Since the respective infectious agents have in common the same route of transmission (oral-fecal route) and since the areas endemic for these diseases greatly overlap, it appears to be advantageous to combine the two valences in the same product. In particular, it will easily be understood that, in the range of vaccines for travelers, an HA-Vi combination is more attractive than the two monovalent HA and Vi vaccines which have to be administered separately.

Studies have already been carried out in order to verify that the HA and Vi valences are compatible in particular in terms of inocuity, of immunogenic power and of stability. These studies use HA-Vi combinations prepared from the monovalent vaccines which already exist on the market; there are essentially two of these studies; firstly, the studies carried out by combining the Havrix™ (HA) and (Vi) monovalent vaccines produced by SmithKline Beecham Biologicals (Rixensart, Belgium) and, secondly, the studies carried out by combining the Avaxim™ (HA) and Typhim Vi™ (Vi) monovalent vaccines produced by Aventis Pasteur (Lyons, France).

In the two series of studies, the monovalent HA vaccine consists of inactivated hepatitis A virus adsorbed onto aluminum hydroxide. Similarly, the monovalent typhoid fever vaccine consists of *Salmonella typhi* capsular polysaccharide which remains nonadjuvanted. Finally, the bivalent combinations are produced in an identical way, by simply mixing the corresponding monovalent vaccines (these monovalent vaccines are marketed in liquid form). Thus, a dose of Avaxim™ and a dose of Typhim Vi™ are mixed together to give a dose of the bivalent HA-Vi combination.

The two series of studies were carried out with combinations made up less than twenty months before giving the injections in the context of clinical trials. These studies showed that the bivalent combinations were equivalent to the corresponding monovalent vaccines, in particular in terms of immunogenic power. Thus, the bivalent combination of SmithKline Beecham Biologicals satisfied the requirements of the British authorities and has already received a marketing authorization in this country. However, this authorization has the restriction of an expiry date set at 12 months after manufacture.

In the field of vaccines, an expiry date of 12 months cannot be considered to be sufficient given, in particular, the time required for controlling the batches before distribution. An expiry date set at 24; or even better, 36 months, greatly facilitates the marketing of the batches.

Now, in the case of the HA-Vi combinations, the applicant has noticed that, beyond 16-18 months past the date of manufacture, the Vi valence gradually loses its immunogenic power, and has put forward a hypothesis regarding the cause of this instability. Specifically, the O-acetyl groups of the Vi polysaccharide, which are characteristic of the immunogenicity of the Vi, hydrolyze over time, especially under alkaline conditions. This hydrolysis is considered to be responsible for the decrease in immunogenic power of the Vi polysaccharide and is thought to be due to the adsorption of the Vi component onto the aluminum hydroxide which is present in the bivalent combination as an adjuvant of the HA valence. The Vi valence immediately adsorbs onto the aluminum gel as soon as the monovalent vaccines are mixed with one another. This adsorption causes the Vi polysaccharide to be maintained in an alkaline environment. Specifically, since the aluminum hydroxide is positively charged, it attracts the OH— ions of the medium, which brings about an increase in the pH in the microenvironment of the aluminum gel in which the Vi is located subsequent to its adsorption. As for the hydrolysis of the O-acetyls, this is a very slow phenomenon, the effects of which are really noticeable after 16-18 months approximately.

Not only has the applicant demonstrated the problem of the instability of the Vi valence over time, but it provides a solution which consists in adding to the bivalent combination a compound which prevents the Vi valence adsorbing onto the aluminum gel, while at the same time maintaining the HA valence in an adjuvanted form. Advantageously, this compound may be an anion, such as a phosphate or citrate ion.

In its most general teaching, the invention therefore relates to an immunization composition comprising at least two valences; (i) a first valence which is adjuvanted with aluminum hydroxide and (ii) a second valence which contains a bacterial capsular polysaccharide comprising one or more O-acetyl groups and which is not adsorbed onto the aluminum hydroxide by virtue of which the first valence is adjuvanted, due to the presence of an additional compound which prevents the adsorption of the second valence onto the aluminum hydroxide, without disturbing the adsorption of the first valence.

According to an advantageous embodiment, the adsorption of the second valence may be prevented by the presence of a protective anionic compound, on condition that it has all the safety guarantees required for use for immunization purposes. This protective compound may be a phosphate, a citrate or a carbonate. It is also possible to use a combination of various anions, for example a combination of phosphate and citrate ions. By way of indication, it is specified that phosphate ions may in particular be provided by a solution containing monopotassium phosphate, disodium phosphate and sodium chloride.

The use of a protective compound in particular makes it possible to stabilize the antigenic activity of the second valence over a long period (24 months or more), preferably during conservation at normal storage temperature or higher (e.g. 37° C.). The stability of the immunogenic activity can be estimated, using various techniques, by measuring this activity at the time the composition is produced and then performing identical measurements over time, or at least 24 months after the date of production, and comparing the results obtained. When the detailed figures are not established as being statistically different from one another, then it should be considered that the immunogenic activity is stable. The immunogenic activity of an antigen can in particular be assayed by the ELISA technique, used commonly in the vaccines field.

The first valence may be any vaccine valence without restriction of type or of structure, on condition of course that it needs to be adjuvanted. Mention is in particular made of the hepatitis A (HepA or HA) valence, the hepatitis B (HepB) valence and the pneumococcus valence. This first valence may consist of an inactivated virus, such as the inactivated HA virus or the inactivated polio virus; an attenuated virus; a viral or bacterial subunit antigen, such as the hepatitis B virus surface antigen, or the diphtheria or tetanus toxoid.

The second valence consists, by definition, of a polysaccharide, which may or may not be conjugated, which contains one or more O-acetyl groups within its repeat unit. The *Salmonella typhi* capsule of polysaccharide (also called Vi polysaccharide) and the *Neisseria meningitidis* group A capsule of polysaccharide satisfy this definition. In these cases, reference is therefore made to Vi or typhoid fever valence and to meningo A valence.

The term "bacterial capsular polysaccharide" is intended to mean a polysaccharide consisting of the chain of the repeat unit characteristic of a capsular polysaccharide, whatever its size and independently of any supplementary modification. The repeat unit of a polysaccharide making up the composition according to the invention necessarily comprises at least one O-acetyl group.

For the purposes of the present invention, the polysaccharide may be obtained in purified form from the bacterium of origin according to entirely conventional techniques. Depending on needs, the polysaccharide may be (i) fragmented or unfragmented and (ii) conjugated or not conjugated to a carrier polypeptide such as diphtheria or tetanus toxoid.

In a more specific context, a subject of the invention is an immunization composition comprising (i) the HA valence adjuvanted with aluminum hydroxide and (ii) the typhoid fever valence consisting of Vi polysaccharide; this being a composition in which the Vi valence is not adsorbed onto the aluminum hydroxide.

For the purposes of the present invention, the first valence may be adjuvanted either by precipitation with the aluminum hydroxide or by adsorption onto the aluminum hydroxide.

The aluminum hydroxide used to adjuvant the first valence may be pure aluminum hydroxide (i.e. an aluminum compound comprising only Al3+ ions and hydroxide groups) or any aluminum known under this name, even if, from a chemical point of view, they do not consist exclusively of aluminum hydroxide. Thus, they may also be mixed aluminum compounds, such as those denoted under the name aluminum hydroxyphosphate or hydroxysulfate. In general, they may be any aluminum compound comprising, in particular, hydroxide groups. By way of illustration, mention may be made of the aluminum hydroxide Alhydrogel™ marketed by the company Superfos Biosector.

The phosphate, citrate, or carbonate ions (protective compound) must be added in sufficient amount to prevent the adsorption of the second valence while at the same time maintaining the first valence in an adjuvanted form. This amount depends on various factors, among which are the amount and nature of the first valence, its adjuvanting method, the amount and nature of the aluminum hydroxide and the amount of the second valence. Those skilled in the art in the field of vaccines are entirely capable of taking these constraints into account in order to determine the suitable amount of the compound preventing the adsorption of the second valence, once the other factors have been established, such that the aluminum hydroxide is saturated with the phosphate ions while at the same time maintaining the first valence in the adjuvanted state.

However, it is specified that the commercial vaccines conventionally contain from 0.6 to 1.5 mg of aluminum/ml. In the commercial HepA vaccines, the alumina gel, present at the conventional doses (expressed as amount of aluminum), is in great excess compared to the HepA antigen since the adsorption sites of the alumina gel are far from being saturated. Thus, in practice, only the amount of aluminum appears to be determinant in establishing the amount of protective compound which must be present.

For a composition according to the invention containing 0.3 mg of aluminum in the form of aluminum hydroxide and in a volume of 0.5 ml, approximately 20 mM of phosphate ions should be added. If the dose of aluminum is doubled in this same volume, twice as many phosphate ions should be added, i.e. 40 mM. However, for a composition according to the invention containing 0.6 mg of aluminum in a volume of 1 ml, 20 mM of phosphate ions is sufficient.

By way of illustration, it is indicated that a bivalent vaccine according to the invention may contain, in a volume of 0.5 ml, (i) 160 antigenic units or 1440 ELISA units of inactivated hepatitis A virus, adsorbed onto (ii) aluminum hydroxide containing 0.3 mg of aluminum; (iii) 0.025 mg of Vi polysaccharide; and (iv) 20 mM of phosphate ions.

The antigenic units and the ELISA units mentioned above are, respectively, units established using reference ELISA assays specific to the companies Aventis Pasteur and SmithKline Beecham Biologicals (van Hoecke et al., J. Travel. Med. (1998) 5: 116 and André et al., in Prog. Med. Virol., Melnick J L Ed, Basle, Karger (1990) 37:72). It cannot be otherwise since there is no standardized reference for the HepA vaccine.

A composition according to the invention is advantageously in a liquid form, and an immunization dose is advantageously formulated in a volume of between 0.5 and 1 ml, inclusive.

A composition according to the invention may be prepared by:
(i) adding phosphate, citrate or carbonate ions to a preparation containing a valence other than the typhoid fever valence, adjuvanted with an aluminum hydroxide; and
(ii) mixing the preparation obtained in point (i) with a preparation containing the typhoid fever valence.

EXAMPLE

Preparation of an HA Vi Composition According to the Invention

A—Preparation of the Adsorbed HA Component 99 ml of a batch of inactivated HA virus, the antigenic titer of which is 885 ELISA U/ml, is mixed with 5.94 ml of 2-phenoxyethanol at 25%. Homogenization is carried out for 15 min and the preparation is then filtered over a Millipak 40 MPGL 04SH2 filter. After filtration, 95 ml of a preparation with a titer of 835 ELISA U/ml are obtained.

47.5 ml of an alumina gel containing 3.14 mg of aluminum/ml are added to this preparation. The volume is made up with 48 ml of 40 mM PBS (Phosphate Buffer). The mixture is stirred overnight at 5° C. (18 hours) in order for the HA component to adsorb onto the alumina gel. The pH is 7.28.

B—Preparation of a 10-Times Concentrated Solution of Vi Polysaccharide

A Vi polysaccharide powder is prepared according to the method of Gotschlich et al., Prog. Immunobiol. Standard (1972) 5:485. 25.1 ml of distilled water prepared for injection (pfi) are poured little by little into a 30 ml flask containing 16.64 mg of Vi (9.5 g % of residual water, i.e. 15.06 mg of dry weight), with continual stirring. The stirring is allowed to continue for 24 hours at 5° C. in order to obtain complete dissolution of the polysaccharide. This preparation is filtered over a 0.22 μm Millex GV SLGV 025 filter. The filter is rinsed with 5 ml of pfi distilled water. The final volume is therefore 30.1 ml.

C—Preparation of the Bivalent HAVi Vaccine 10.6 ml of a 94 mM phosphate solution, followed by 8.1 ml of the preparation obtained in point B) (Vi), are added to 62 ml of the preparation obtained in point A (HA). The characteristics of the vaccine thus obtained are as follows:

Final phosphate concentration: 20 mM
pH: 7.3
Osmolarity: 578 mosm/kg

This preparation, named preparation P2; is then divided up into 0.5 ml doses.

In parallel, two other bivalent compositions, P2' and P2", were also prepared, no longer containing 20 mM of phosphate, but 10 and 40 mM of phosphate, respectively. To do this, 10.6 ml of a phosphate solution at 17.6 mM or 246 mM, depending on the species, are added.

The behavior of the HA and Vi components in the P2; P2' and P2" compositions was immediately studied by assaying these components, by ELISA, in the compositions without further manipulation or after centrifugation. It was noted that, at 10 mM of phosphate, the HA remained adsorbed but Vi adsorbed onto the alumina gel, whereas, at 40 mM of phosphate, the Vi no longer adsorbed but the HA partially desorbed. At 20 mM of phosphate, the desired conditions are satisfied: the HA remains adsorbed whereas the Vi does not adsorb.

Subsequently, the stability of the P2 doses was studied at 5° C.±3° C. for 30 months. The antigenic capacity of the Vi polysaccharide in the immunization doses taken in their entirety, and in the supernatant after centrifugation (the component adsorbed onto the alumina gel sediments with the gel), was in particular evaluated by ELISA; this also makes it possible to establish the percentage of Vi not adsorbed.

The indirect ELISA method is used. The Vi antigen to be assayed is sandwiched between anti-Vi antibodies covering the bottom of a plate and mouse anti-Vi antibodies. A biotinylated anti-mouse-IgG antibody is added, followed by the horseradish peroxidase-coupled biotinylated streptavidin complex. The reaction is revealed by adding the substrate orthophenylenediamine dihydrochloride (OPD). The degradation of the OPD causes an orangy-brown coloration proportional to the amount of Vi antigen. Its intensity is measured on a spectrophotometer.

100 µl of an anti-*Salmonella typhi* serum are distributed into 96-well plates. This is left to incubate for 5 hours at 37° C. and then the plate is emptied and 3 washes in PBS (phosphate buffer) containing 0.05% Tween are carried out. The free sites are saturated by adding 200 µl of a solution of powdered milk diluted in PBS. Incubation is performed for 1 hr 30 minutes at 37° C. and then the plate. is emptied and 3 washes are performed. Doubling serial dilutions of a standard vaccine are prepared so as to obtain a standard range. The doses of vaccine to be assayed and also a reference dose (which makes it possible to verify the calibration range) are suitably diluted; 100 µl of each dilution are distributed into the cupules and left to incubate overnight at 37° C. The plate is emptied and washes are performed. 100 µl per cupule of an anti-Vi mouse serum, suitably diluted, are then added. This is left to incubate for 1 hr at 37° C. and then the plate is emptied and washes are performed. Biotinylated anti-mouse immunoglobulins are then attached (100 µl per cupule of a suitable dilution). This is left to incubate for 1 hour at 37° C. and then the plate is emptied and washes are performed. Peroxidase-coupled biotinylated streptavidin is then attached (100 µl per cupule of a suitable dilution). This is left to incubate for 1 hour at 37° C. and then the plate is emptied and washes are performed. The plate is developed by adding 100 µl per cupule of a solution of OPD at 1 mg/ml in citrate phosphate buffer, pH 5. This is left to incubate for 30 min at ambient temperature in the dark before adding 100 µl of 2 N sulfuric acid to the cupules. The plate is read on a spectrophotometer at 492 nm. The standard curve of absorbance as a function of concentration is established. The titer of each of the dilutions assayed is calculated relative to the standard curve and is expressed in ng/ml. In order to obtain the mean titer for each immunization dose assayed, the mean of the titers obtained with all the dilutions is calculated. The titer is given a µg/dose.

The amount of Vi polysaccharide O-acetyls present in the supernatant, after certification, was also measured. The O-acetyls are titered with a colorimetric method using hydroxylamine (Hestrin S. J. Biol. Chim. (1949) 180: 249). Hydroxylamine in alkaline medium forms, with esters, a hydroxamic acid which, in the presence of ferric salt, gives a brown coloration, the intensity of which is measured on a spectrophotometer at 540 nm.

In parallel, an identical study was carried out with a preparation termed preparation P1; prepared in the same way as P2; with the only difference being that phosphate is not added at the time the bivalent vaccine is made up. In this case, the Vi component immediately adsorbs onto the alumina gel and, in order to assay it after centrifugation, as for P2; it should be desorbed beforehand. This desorption is obtained by modifying the pH and the ionic strength of the medium. After centrifugation, the alumina gel is brought into contact with a 150 mM trisodium citrate solution for 6 hours at 37° C. The mixture is then centrifuged in order to collect the supernatant in which the Vi component is found.

The results are given in Table I below.

TABLE I

| | 5° C. | | T0 | 3 months | 6 months | 9 months | 12 months | 18 months | 24 months | 30 months |
|---|---|---|---|---|---|---|---|---|---|---|
| Vi in the whole vaccine | Vi ELISA (·g/dose) | P2 | 23.6 | 25.5 | 21.7 | 21.3 | 18.5 | 23.7 | 24.3 | 26.5 |
| | | P1 | 24.4 | 23.3 | 22.2 | 19.8 | 17.9 | 20.5 | 18.6 | 19.3 |
| Vi in the supernatant after centrifugation | Vi ELISA (·g/dose) | P2 | 24.3 | 26 | 23.1 | 21.8 | 17.9 | 25 | 21.9 | 25.8 |
| | | P1 | 21 | 16.9 | 16.5 | 15.4 | 12 | 14.7 | 21.8 | 15.7 |
| | O-acetyls (·mol/dose) | P2 | 0.127 | 0.148 | 0.116 | 0.117 | 0.130 | 0.134 | 0.095 | 0.143 |
| | | P1 | 0.081 | 0.056 | 0.055 | 0.055 | 0.061 | 0.057 | 0.090 | 0.054 |
| | Polysaccharides (·g/dose) | P2 | 32.5 | 30.5 | 27.6 | 31 | 30.4 | 29.1 | 31.7 | 29.3 |
| | | P1 | 20.8 | 22 | 15.6 | 16.2 | 18.5 | 16.5 | 17 | 18.4 |
| % desorption of the Vi in P1 | | | | 86% | 72% | 74% | 78% | 67% | 72% | 63% | 81.6% |

The stability of the P2 formulation was also studied at 25° C.±2° C. for 6 months and at 37° C.±3° C. for 3 months. The results are given in Tables II and III below.

TABLE II

| 25 ° C. | | | T0 | 1 month | 3 months | 6 months |
|---|---|---|---|---|---|---|
| Vi in the whole vaccine | Vi ELISA (µg/dose) | P2 | 23.6 | 23.6 | 21.7 | 20.6 |
| | | P1 | 24.4 | 19.6 | 11.3 | 7.4 |
| Vi in the supernatant after centrifugation | Vi ELISA (µg/dose) | P2 | 24.3 | 25.5 | 22.6 | 20.1 |
| | | P1 | 21 | 15 | 10.3 | 6.3 |
| | O-acetyls (µmol/dose) | P2 | 0.127 | 0.130 | 0.103 | 0.137 |
| | | P1 | 0.081 | 0.053 | 0.041 | 0.029 |
| | Poly-saccharides (µg/dose) | P2 | 32.5 | 31.6 | 25.5 | 27.2 |
| | | P1 | 20.8 | 17.3 | 10.3 | 6.3 |
| % desorption of the Vi in P1 | | | | 86% | 77% | 91% | 85% |

TABLE III

| 37° C. | | | T0 | 1 month | 3 months |
|---|---|---|---|---|---|
| Vi in the whole vaccine | Vi ELISA (µg/dose) | P2 | 23.6 | 24.1 | 21 |
| | | P1 | 24.4 | 12.7 | 5.6 |
| Vi in the supernatant after centrifugation | Vi ELISA (µg/dose) | P2 | 24.3 | 25.5 | 21.1 |
| | | P1 | 21 | 9.9 | 4.7 |
| | O-acetyls (µmol/dose) | P2 | 0.127 | 0.143 | 0.104 |
| | | P1 | 0.081 | 0.050 | 0.026 |
| | Polysaccharides (µg/dose) | P2 | 32.5 | 36 | 22.5 |
| | | P1 | 20.8 | 15.4 | 9.9 |
| % desorption of the Vi in P1 | | | | 86% | 78% | 84% |

The invention claimed is:

1. An immunization composition comprising (i) a first valence adjuvanted with an aluminum compound comprising hydroxide groups, (ii) a second valence comprising a bacterial capsule polysaccharide comprising one or more O-acetyl groups, and (iii) phosphate, citrate, and/or carbonate ions in an amount sufficient to prevent adsorption of the second valence onto the aluminum compound, wherein the first valence is hepatitis A valence and the second valence is a typhoid fever *Salmonella typhi* capsular Vi polvsaccharide.

2. The composition of claim 1 wherein the hepatitis A valence is inactivated hepatitis A virus.

3. The composition of claim 1 or 2 wherein the typhoid fever valence has a stable antigenic titer for at least 24 months.

4. The composition of claim 1 or 2 wherein the first valence is adjuvanted with an aluminum compound which is aluminum hydroxide or aluminum hydroxyphosphate.

5. The composition of claim 1 or 2 wherein the first valence is adjuvanted by adsorption onto an aluminum compound.

6. A method for manufacturing the composition of claim 1 the method comprising:
 (a) adding phosphate, citrate, and/or carbonate ions to a preparation comprising a first valence adjuvanted with an aluminum compound comprising hydroxide groups; and
 (b) mixing the preparation obtained in step (a) with a preparation comprising a second valence comprising a bacterial capsular polysaccharide comprising one or more O-acetyl groups,
wherein the amount of phosphate, citrate or carbonate ions added is sufficient to prevent adsorption of the second valence onto the aluminum compound, and
wherein the first valence is hepatitis A valence and the second valence is typhoid fever *Salmonella typhi* capsular Vi polvsaccharide.

7. The method of claim 6 wherein the hepatitis A valence is inactivated hepatitis A virus.

8. The method of claim 6 wherein the typhoid fever valence has a stable antigenic titer for at least 24 months.

9. The method of claim 6 wherein the first valence is adjuvanted with an aluminum compound which is aluminum hydroxide or aluminum hydroxyphosphate.

10. The method of claim 6 wherein the first valence is adjuvanted by adsorption onto an aluminum compound.

* * * * *